United States Patent [19] [11] 4,269,066
Fischer [45] May 26, 1981

[54] ULTRASONIC SENSING APPARATUS

[76] Inventor: Christopher L. Fischer, 1438 Wildrose Way, Mountain View, Calif. 94040

[21] Appl. No.: 67,115

[22] Filed: Aug. 16, 1979

[51] Int. Cl.³ .................. A61B 10/10; G01N 29/00
[52] U.S. Cl. .................................. 73/639; 128/660
[58] Field of Search ............... 73/639, 621, 626, 641; 128/660

[56] References Cited

U.S. PATENT DOCUMENTS

| 3,415,111 | 12/1968 | Chattaway et al. | 73/622 X |
| 3,423,993 | 1/1969 | Lynnworth | 73/639 |
| 3,577,772 | 5/1971 | Perilhou | 128/660 |
| 3,693,415 | 9/1972 | Whittington | 73/626 X |
| 3,938,502 | 2/1976 | Bom | 73/626 X |
| 4,034,744 | 7/1977 | Goldberg | 128/660 |
| 4,143,554 | 3/1979 | Nagy et al. | 73/641 |
| 4,163,394 | 8/1979 | Soldner | 73/626 |
| 4,181,120 | 1/1980 | Kunii et al. | 128/660 |
| 4,210,028 | 7/1980 | Hildebrand | 73/626 X |
| 4,231,373 | 11/1980 | Waxman et al. | 128/660 |
| 4,233,988 | 11/1980 | Dick et al. | 128/660 |

FOREIGN PATENT DOCUMENTS

| 1121903 | 7/1968 | United Kingdom | 73/639 |
| 1359187 | 7/1974 | United Kingdom | 73/639 |
| 1428370 | 3/1976 | United Kingdom | 73/639 |

Primary Examiner—Daniel M. Yasich
Attorney, Agent, or Firm—Blakely, Sokoloff, Taylor & Zafman

[57] ABSTRACT

An ultrasound sensing apparatus suitable for human body scanning, particularly regions which are difficult to scan with larger ultrasound heads. The ultrasound transducers are mounted for rotation in an off-axis configuration. With this configuration, transmission and reception of sound occurs without the sound being normal to the membrane contacting the body. This eliminates reverberation problems and permits viewing of shallow tissue with a relatively small apparatus.

13 Claims, 6 Drawing Figures

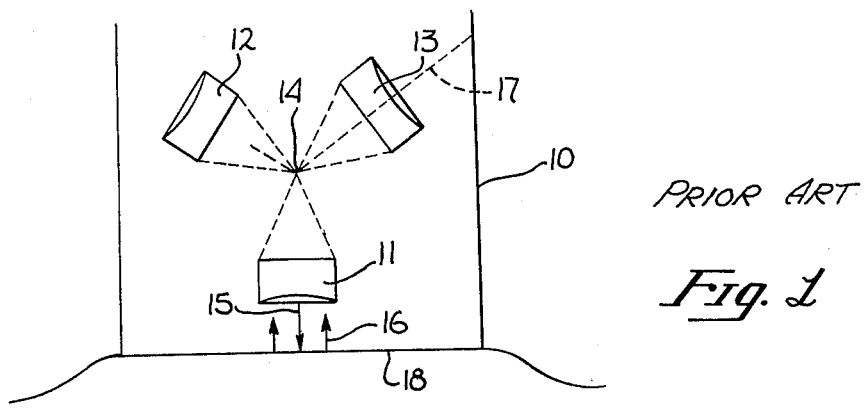
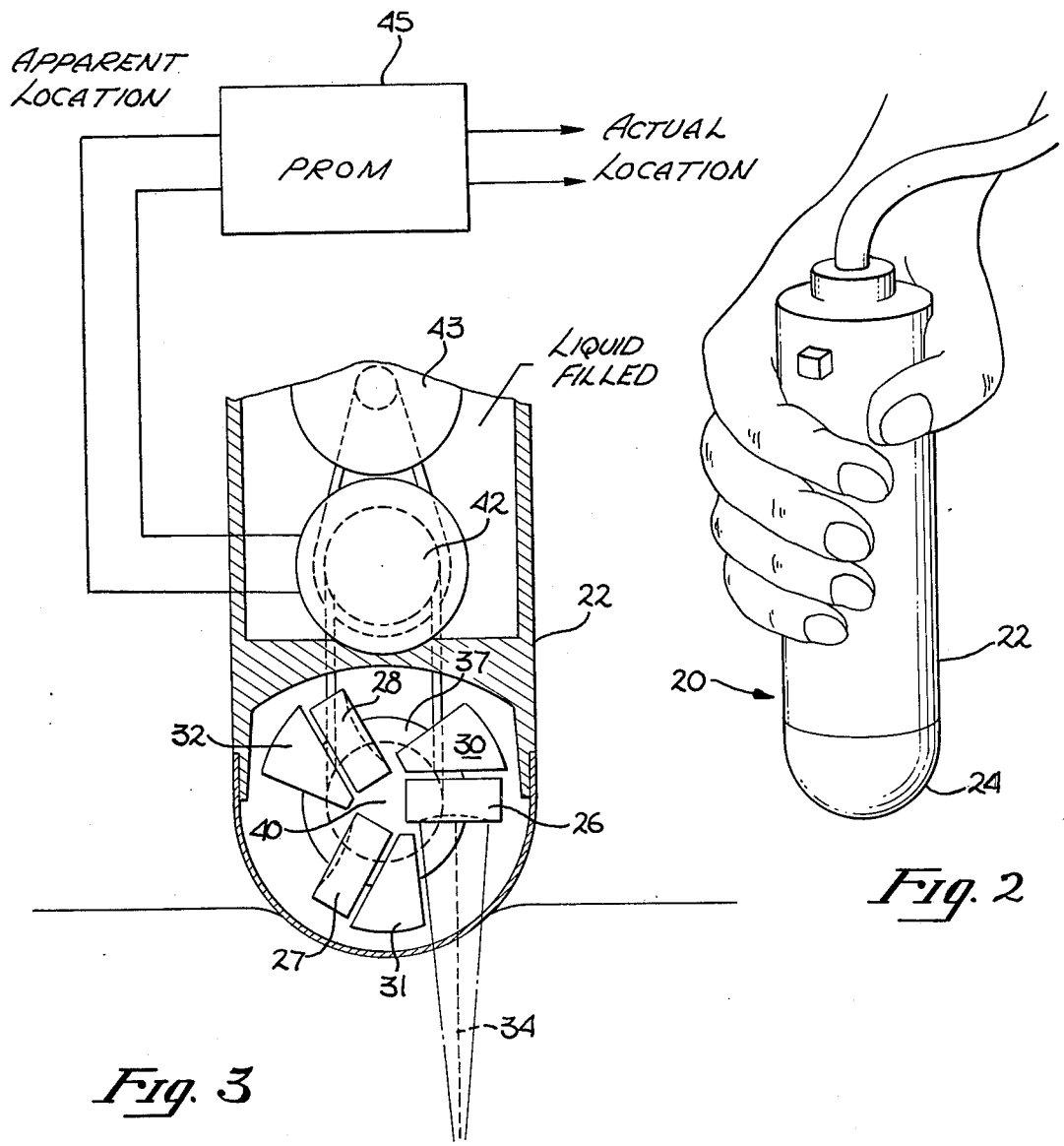

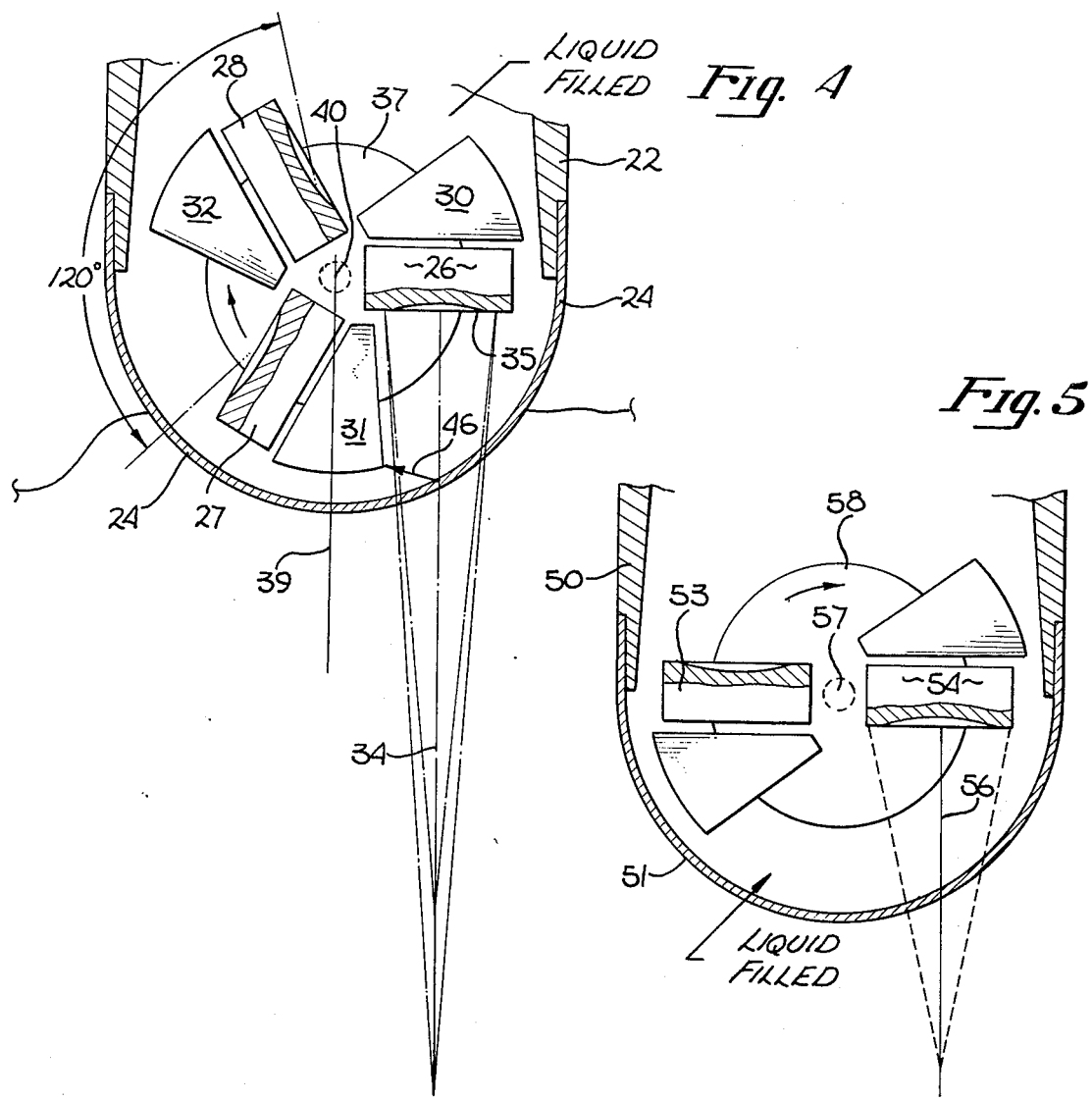
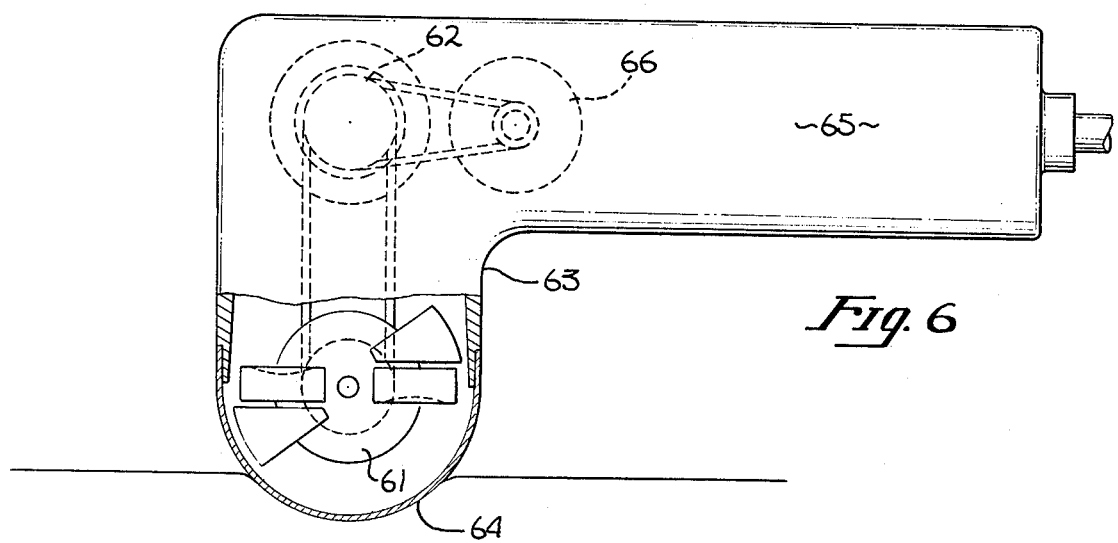

ULTRASONIC SENSING APPARATUS

BACKGROUND OF THE INVENTION

1. Field of the Invention

The invention relates to the field of ultrasonic imaging, and in particular to ultrasonic imaging heads with rotating transducers.

2. Prior Art

In recent years, more emphasis has been placed on the use of ultrasonics to provide anatomical images of soft body tissue. This emphasis, to some extent, resulted from a public awareness of the dangers of x-rays, and also from the technical advances made in electronics. In the latter category, currently available integrated circuit memories, microprocessors, etc., have made possible the processing of signals which would not have been attempted a decade ago.

Numerous ultrasound scanners are commercially available which include a scanning head which is brought in contact with the human body. One or more ultrasound transducers transmit pulses of ultrasound and then sense the echoes which are displayed or recorded. High quality images are obtained, particularly where relatively large imaging heads are used. In many applications, however, smaller imaging heads are required to scan certain tissue. For example, a smaller imaging head or apparatus is required to view under the ribs for gall bladder images or to examine thyroid tissue.

One apparatus currently employed for scanning these more difficult regions includes a plurality of transducers which are rotated about a common axis where each transducer sequentially scans the body. A problem associated with this device (caused by reverberations) is described in conjunction with FIG. 1. A typical transducer with this configuration is described in U.S. Pat. No. 4,149,419.

As will be seen, the present invention provides an imaging head employing a plurality of transducers arranged in an off-axis configuration. This configuration eliminates the reverberation problems found in prior art devices.

BRIEF DESCRIPTION OF THE DRAWINGS

FIG. 1 is a diagram illustrating the mounting of three transducers in an imaging head built in accordance with the prior art.

FIG. 2 is a perspective view of an imaging head built in accordance with the present invention.

FIG. 3 is a cross-sectional elevation view of a portion of the imaging head of FIG. 2. Also illustrated in FIG. 3 is the interconnection of an encoder in the head with a programmable read-only memory.

FIG. 4 is a partial exploded view of the imaging head of FIG. 2.

FIG. 5 is a cross-sectional elevation view of an alternate embodiment of an imaging head built in accordance with the present invention employing two transducers; and FIG. 6 is an alternate embodiment of the present invention which illustrates an alternate configuration for the overall shape of the imaging head.

SUMMARY OF THE INVENTION

An ultrasound sensing apparatus for scanning the human body is described. The apparatus includes a rotating member having an axis of rotation. A plurality of ultrasonic transducers, each having a beam axis along which ultrasound is transmitted and received, are mounted for rotation on the rotating member. Each of the beam axes of these transducers are mounted such that they do not intersect the axis of rotation of the member. These beam axes lie in a common plane perpendicular to this axis of rotation. As the transducers are rotated, their beam axes sequentially cross a membrane or window which is in contact with the body. Because of the off-axis mounting of these transducers on the rotating member, the beam axes are not normal to thebody when they are activated. This substantially eliminates the reverberation problems associated with similar prior art imaging devices.

DETAILED DESCRIPTION OF THE INVENTION

An ultrasonic sensing apparatus or imaging head suitable for human body scanning and particularly suitable for scanning body areas requiring a small imaging head is disclosed. In the following description, numerous specific details, such as specific frequencies, etc., are set forth in order to provide a thorough understanding of the present invention. It will be obvious to one skilled in the art that the invention may be practiced without these specific details. In other instances, well-known devices and components are not described in detail in order not to obscure the present invention in unnecessary detail.

Referring first to FIG. 1, in a typical prior art imaging head, a plurality of transducers are mounted for rotation within a housing 10. The transducers 11, 12 and 13 are mounted for rotation about the axis 14. The beam axis for each of the transducers, that is, the axis along which transmission and reception occur, passes through the axis of rotation. For example, the axis 17 for the transducer 13 intersects the axis of rotation 14.

In this typical prior art device, the transducers are each sequentially activated as they rotate by the window 18. The window is in contact with the body. When the beam axes of these transducers are normal to the body or window, or substantially normal to the body or window, echoes occur from this interface which are sensed by the transducer. As shown in FIG. 1, for the position of transducer 11, ultrasound 15 from the transducer 11 is reflected at the interface, causing the echo 16. The sound 16 is reflected from the face of the transducer 11 and again rebounds from the interface. This continuing rebounding causes periodic artifacts in the observed image. Note that this problem of reverberations occurs when the transducer 11 is in a normal or substantially normal position with respect to the interface. In the other positions, the reflections from the interface are not directed back to the transducer.

To solve this problem in the prior art, often the echoes associated with the first few centimeters beyond the interface are ignored to eliminate the echoes from the first interface rebound. This has the obvious problem that tissue near the skin cannot be scanned. In some instances, the transducers are mounted at a distance from the interface greater than the maximum body depth which is to be scanned. When this is done, the echoes from body tissue are received before the second rebound, thus eliminating the reverberation problem except for the first rebound. However, this approach requires a relatively large imaging head which is unsuited for certain types of scanning, such as under the ribs or for scanning the thyroid.

Referring now to FIG. 2, the invented imaging head, in its presently preferred embodiment, is contained within a generally cylindrical housing 22 which includes a hemispheric shaped window or membrane 24 for contacting the body. With this shape, the membrane 24 may be readily urged onto the body for scanning more difficult regions.

As shown in FIGS. 3 and 4, the imaging head includes a rotating member 37 having an axis of rotation 40 on which the ultrasound transducers 26, 27 and 28 are mounted. The rotating member 37 is driven through a belt drive from a motor 43. The position of the member 37 as it rotates is indicated by the mechanical encoding device 42 which is driven in synchronous with the rotating member 37.

Each of the transducers includes a beam axis along which it transmits and received ultrasound. The beam axis 34 for the transducer 26 is illustrated for discussion purposes. The transducers are mounted such that their beam axes are offset or spaced-apart from the axis of rotation 40. Unlike the prior art of FIG. 1 where the beam axes cross the axis of rotation, note that the beam axis 34 does not intersect the axis of rotation 40. In the presently preferred embodiment, all of the beam axes lie in a common plane which is perpendicular to the axis of rotation 40. Also, the transducers are evenly spaced about the axis 40 and for the embodiment employing three transducers, they are spaced apart (from each other) by 120°.

Rubber baffles are mounted on the rotating member 37 adjacent to the non-active end of each of the transducers. For example, the baffle 30 is disposed opposite the face 35 of the transducer 26. Similarly, the baffles 31 and 32 are disposed adjacent to the non-active ends of the transducers 27 and 28, respectively. These baffles are employed to reduce the transmission of unwanted ultrasound within the imaging head.

In the presently preferred embodiment, the window or membrane 24 is hemispheric in shape and has its radius originating on the axis 40. A semi-rigid membrane having a thickness of approximately ½ the wavelength of the ultrasound is employed. Also in the presently preferred embodiment, the volume defined by the housing 22 and membrane 24 is liquid-filled. For a discussion of the membrane thickness and accoustic properties of the liquid, see co-pending application Ser. No. 925,701 filed July 18, 1978, and now U.S. Pat. No. 4,231,373 entitled, "ULTRASONIC IMAGING APPARATUS", and assigned to the assignee of the present invention.

In the presently preferred embodiment, commercially available transducers are employed having a diameter of approximately 13 mm and a center frequency of approximately 3.5 MHz. A pulse rate of approximately 3 KHz is used. The transducers are rotated at approximately 6.6 revolutions per second within the liquid-filled housing.

As is well-known, the transducers are sequentially activated as each of their beam axes cross the membrane 24. Thus, for example, for the positions of the transducers shown in FIGS. 3 and 4, transducer 26 is activated and transducers 27 and 28 are off. As rotation continues, then transducer 28 is activated, and so on. In the presently preferred embodiment, where three transducers are employed, each transducer is activated when it is in the position of transducer 26 (−90° from axis 39). The transducers are deactivated at approximately 15° beyond the axis 39. Thus, there is approximately 45° of "dead-time" in each rotation of the rotating member.

Importantly, it should be noted that because of the offset configuration of the transducers, the beam axes of the transducers are never normal or substantially normal to the interface of the imaging head and the body. Note, for example, that the beam axis 34 is not normal or perpendicular to the membrane 24, nor will it be as it rotates about the axis 40. This is in sharp contrast to the prior art illustrated in FIG. 1 where each of the transducers for the position shown by transducer 11 is normal to the interface. By having the offset configuration as illustrated, echoes from the interface are directed away from the receiving face of the transducers. For example, as shown by echo 46 of FIG. 4, the sound returned from the interface is directed away from the receiving face 35 of the transducer 26 and, to a large extent, is absorbed by the baffle 31.

The echoes received from the transducers may be processed in any one of a number of well-known ways to produce visual images of the body tissue.

In the presently preferred embodiment, a programmable read-only memory (PROM) 45 shown in FIG. 3 is used as a calibration device. The encoder 42 provides a digital signal indicating the instantaneous angular position of the rotating member 37. From this information the expected position of the beam axis of each of the transducers is known. However, the beam axes of these transducers are seldom in alignment with the transducer body. Typical specifications for commercially available transducers indicate a tolerance of ±1° for the difference between the actual beam axis and the central axis of these transducers. The PROM 45 is programmed after the transducers are mounted on the rotating member 37. As the rotating member is rotated, the actual position of the beam axis is noted and compared to the angular position of the member 37. This data is stored within the PROM 45. The output of the encoder 42 is used to address the PROM, that is, to seek out the data in a particular location with the PROM 45. Stored at this location is the actual beam location which is provided as an output signal from the PROM 45. Thus, after the manufacturing of each of the imaging heads, a PROM is programmed which acts as a calibration means for that particular head.

While in the presently preferred embodiment three transducers are employed, other numbers of transducers may likewise be employed which are offset from the axis of rotation. In FIG. 5, a housing 50 is shown which includes a membrane 51. A rotating member 58 which rotates about the axis 57 includes a pair of evenly spaced transducers 53 and 54. Again, the beam axes of these transducers, such as axis 56 of transducer 54, are offset from the axis 57. The beam axes of the transducers in this embodiment again lie in a common plane which is perpendicular to the axis 57. It should be noted that when fewer transducers are employed, more "dead-time" occurs.

In FIG. 6, another embodiment is illustrated with an L-shaped housing. The housing 63 includes a handle section 65 and a membrane 64. For purposes of illustration, two transducers are shown offset on the rotating member 64 which is driven by the motor 66. Also, an encoder 62 is illustrated in this embodiment. For some body areas, having the membrane at a right angle to the handle provides for easier scanning.

Thus, an imaging head has been described which employs a plurality of rotating transducers. By offsetting these transducers from their axis of rotation, the ultrasound propagating to and from the transducer face is never perpendicular to the body/head interface. This eliminates the reverberation problems common with prior art devices.

I claim:

1. An ultrasound sensing apparatus comprising:
   a plurality of ultrasound transducers each having a beam axis;
   a rotating member for receiving said transducers, said member having an axis of rotation, said transducers being mounted on said member such that said beam axis of each of said transducers is spacedly offset from and non-intersecting with, said axis of rotation; and
   a housing for receiving said transducers and said rotating member, said housing including a transmission window through which said beam axis of each of said transducers sequentially crosses as said member rotates about said axis of rotation;
   each of said transducers being selectively actuated, whereby ultrasound associated with said transducers passes through said window without being normal to said window.

2. The apparatus defined by claim 1 wherein said beam axes of said transducers lie in a common plane which plane is perpendicular to said axis of rotation.

3. The apparatus defined by claim 2 wherein said transducers are evenly spaced about said axis of rotation.

4. The apparatus defined by claim 3 wherein said window generally defines a hemisphere having a center on said axis of rotation.

5. The apparatus defined by claim 4 wherein the interior of said housing which includes said transducers is liquid filled.

6. The apparatus defined by claim 2 including a position indicating means coupled to said rotational member for providing a digital output representative of the indicated position of said transducers as they rotate about said axis of rotation.

7. The apparatus defined by claim 6 including a memory, said digital output of said position indicating means being coupled to said memory for addressing said memory, said memory containing data representative of the actual position of said beam axes of said transducers as a function of said indicated position, whereby said memory provides position calibration.

8. An ultrasonic sensing apparatus for body contact scanning comprising:
   a housing;
   a rotating member, disposed within said housing, having an axis of rotation about which said member rotates;
   a plurality of ultrasonic transducers each having a beam axis along which ultrasound is transmitted and received, said transducer being mounted for rotation on said member such that each of said beam axes are spacedly offset from and non-intersecting with said axis of rotation and lie in a common plane perpendicular to said axis of rotation;
   each of said transducers being selectively actuated, whereby sensing occurs without said beam axes being normal to the body.

9. The apparatus defined by claim 8 wherein said transducers are evenly spaced about said rotating member.

10. The apparatus defined by claim 9 wherein said housing has a generally elongated cylindrical shape, terminating in one end in a hemispheric-shaped membrane, said membrane having a center which is on said axis of rotation.

11. The apparatus defined by claim 10 wherein said rotating member is mounted within said housing such that said beam axes of said transducer sequentially intersect said membrane as said member rotates.

12. The apparatus defined by claim 9 including a digital encoder for providing digital signals representative of the sensed positions of said rotating member.

13. The apparatus defined by claim 12 including a programmable read-only memory coupled to receive said digital signals as an address for said memory, said memory programmed with calibration data so as to provide output signals representative of the actual beam axes positions of said transducers as a function of said sensed positions.

* * * * *